United States Patent
Feng

(10) Patent No.: US 6,602,401 B1
(45) Date of Patent: Aug. 5, 2003

(54) AMPEROMETRIC SENSOR FOR LOW LEVEL DISSOLVED OXYGEN WITH SELF-DEPLETING SENSOR DESIGN

(75) Inventor: Chang-Dong Feng, Long Beach, CA (US)

(73) Assignee: Rosemount Analytical Inc., Irvine, CA (US)

( * ) Notice: Subject to any disclaimer, the term of this patent is extended or adjusted under 35 U.S.C. 154(b) by 1 day.

(21) Appl. No.: 09/707,740

(22) Filed: Nov. 1, 2000

(51) Int. Cl.[7] .............................................. G01N 27/404
(52) U.S. Cl. ....................................... 205/783; 204/415
(58) Field of Search ........................ 204/415; 205/782.5, 205/783

(56) References Cited

U.S. PATENT DOCUMENTS

| | | | |
|---|---|---|---|
| 3,718,566 A | * 2/1973 | Krebs | |
| 3,948,746 A | 4/1976 | Poole | 204/195 P |
| 4,003,705 A | * 1/1977 | Buzza et al. | |
| 4,078,981 A | 3/1978 | Neti et al. | 204/195 P |
| 4,207,161 A | 6/1980 | Pegnim | 204/195 P |
| 4,450,064 A | 5/1984 | Harman, III | 204/412 |
| 4,486,291 A | 12/1984 | Schindler et al. | 204/415 |
| 4,620,918 A | 11/1986 | Bukamier et al. | 204/403 |
| 4,772,375 A | * 9/1988 | Wullschleger et al. | |
| 4,776,942 A | 10/1988 | Neti et al. | 204/415 |
| 4,900,422 A | 2/1990 | Bryan et al. | 204/401 |
| 4,956,063 A | 9/1990 | Hale | 204/153.17 |
| 5,098,547 A | 3/1992 | Bryan et al. | 204/401 |
| 5,239,257 A | 8/1993 | Muller et al. | 324/71.1 |
| 5,384,029 A | 1/1995 | Campbell | 204/415 |
| 5,527,444 A | 6/1996 | Sweeney, Jr. | 204/415 |
| 5,723,769 A | 3/1998 | Barber et al. | 73/19.12 |
| 5,728,290 A | 3/1998 | Xie et al. | 205/783 |
| 6,030,827 A | 2/2000 | Davis et al. | 435/287.1 |
| 6,068,748 A | 5/2000 | Berger | 204/426 |
| 6,080,294 A | 6/2000 | Shen et al. | 204/415 |

FOREIGN PATENT DOCUMENTS

| | | |
|---|---|---|
| JP | 08 233775 A | 9/1996 |
| JP | 2000 074871 | 3/2000 |

OTHER PUBLICATIONS

"Free Residual Chlorine, Dissolved Oxygen, and Dissolved Ozone Amperometric Sensors", Rosemount Analytical Product Data Sheet Models 499A CL, DO, OZ, Nov. 1998, pp. 1–6.
"Dissolved Oxygen Measurement in Municipal Waste Treatment", Rosemount Analytical Application Data Sheet, Oct. 1998, 2 pages.
"Dissolved Oxygen Measurement in Oceans, Lakes and Rivers", Rosemount Analytical Application Data Sheet, Dec. 1998, 2 pages.
"Liquid Analysis Instrumentation", Rosemount Analytical, Uniloc Division Brochure, Apr. 1998, 16 pages.
"Dissolved Oxygen Sensor", Rosemount Analytical Model 430 Product Data Sheet 71–430, Mar. 1996, pp. 1–4.
"Free Residual Chlorine, Dissolved Oxygen and Dissolved Ozone Amperometric Sensors", Rosemount Analytical Instruction Manual Models 499A CL, DO, OZ, Jun. 1998, 28 pages.
"Dissolved Oxygen Sensor", Rosemount Analytical Instruction Manual Model 430 DO, May 1996, 22 pages.

* cited by examiner

*Primary Examiner*—T. Tung
(74) *Attorney, Agent, or Firm*—Westman, Champlin & Kelly

(57) ABSTRACT

A dissolved oxygen sensor having a cathode and anode immersed in an electrolyte is designed to provide a low background current in the sensor when a potential is applied to the cathode. The background current is maintained at a desired level by selecting the area and length of a channel or path of diffusion of residual oxygen in the electrolyte to the cathode. The area (A) of the diffusion channel in relation to its length (L) is selected to be at or below a selected ratio, A/L.

7 Claims, 3 Drawing Sheets

AMPEROMETRIC SENSOR FOR LOW LEVEL DISSOLVED OXYGEN WITH SELF-DEPLETING SENSOR DESIGN

BACKGROUND OF THE INVENTION

The present invention relates to a sensor to sense dissolved oxygen (DO) in boiler water, and the like, for determining purity of the water. The sensor provides an output current and the present invention teaches reducing background or offset current of the sensor to improve the ability to sense low levels of oxygen in water by controlling the configuration of an internal oxygen diffusion path of residual oxygen in a liquid electrolyte used for the sensor.

The amount of dissolved oxygen in aqueous solutions such as water is a direct indication of water quality for power plant corrosion control applications. The prior art dissolved oxygen sensors are enclosed in a housing that protrudes into a flowing stream or sample of the water and when energized with an electrical potential the oxygen in the water or other liquid will pass through a gas permeable membrane to a component of the sensor, called a cathode.

The gas permeable membrane of prior art sensors cover the sensor components, which are in an outer housing. The cathode which is normally gold, and a silver anode are mounted at spaced locations in the housing. An electrolyte solution, such as potassium chloride, immerses the cathode and anode.

When the sensor does start to operate, that is, when an oxygen reduction potential is applied to the cathode, the oxygen in the electrolyte stored in a chamber in the sensor housing diffuses into a film of electrolyte between the membrane and the cathode. Oxygen in the vicinity of the cathode gets reduced through the following known electrochemical process:

$$O_2 + 2H_2O + 4e \rightarrow 4OH^- \quad (1)$$

The process creates an oxygen concentration gradient around the cathode which generates a diffusion of residual dissolved oxygen contained in the liquid electrolyte in the sensor chamber toward the cathode. At steady state a constant residual oxygen flux reaches the cathode and creates the constant background or offset current. The current from constant residual oxygen flux follows Fick's First Law, and the background current $I_b$ can be expressed as:

$$I_b = 4FSDAP/L. \quad (2)$$

In the above equation (2), F is the Faradaic constant; S the oxygen solubility; D the diffusion coefficient of oxygen through the electrolyte; A the cross sectional area of the diffusion flux, or essentially the cross sectional area of the channel between the cathode and the electrolyte chamber; P the partial pressure of oxygen in air; and L the diffusion channel length. In equation (2) above all of the values of the factors at the right are known. At room temperature F is 95600C/mole, SD was tested to be $5 \times 10^{-10}$ mole/atm.m.s, and P is 0.21 atm.

A, the area of the channel or path provided for diffusion of oxygen flux from the electrolyte chamber to the cathode, and L, the diffusion path length both can be changed through sensor design.

The residual oxygen thus causes an output current, even when the sensor is exposed to oxygen-free media.

When the sensor is used for sensing oxygen in water (or other aqueous solutions) to be monitored the membrane is exposed to the water and dissolved oxygen in the water is also attracted to the cathode and diffuses through the membrane to the film of electrolyte between the membrane and the cathode and then to the cathode.

The output current from dissolved oxygen in water being sampled, above the background or offset current of the sensor, is directly proportional to the oxygen partial pressure in the water, or in other words, proportional to the concentration of dissolved oxygen in the water.

To achieve sensitivity to low levels of dissolved oxygen in the water, in the range of a few parts per billion (ppb), the background or offset current of the sensor must be low. The background current is mostly contributed from the dissolved oxygen that remains in the electrolyte stored in the sensor, which has been termed the residual oxygen. One prior art method to reduce the background current has been to use an extra electrode guard ring to deplete the residual oxygen around the cathode electrochemically during the sensor operation. This adds cost and parts to the sensor.

The residual oxygen cannot be eliminated from the electrolyte. So the problem is to reduce the background current caused by the residual oxygen in the electrolyte with a simple, low cost construction, without sacrificing performance for measuring dissolved oxygen in water samples.

SUMMARY OF THE INVENTION

The present invention relates to a dissolved oxygen sensor that maintains the background current at a very low level while also maintaining the desired sensitivity by controlling the ratio of the area (A) to the length (L) of the channel for diffusion of residual oxygen from an electrolyte in a sensor chamber to a cathode. When the A/L ratio is small enough, the cathode will deplete the residual oxygen around it. Thus, the present invention results in a self-depleting dissolved oxygen sensor.

The A/L ratio is selected to be at or below a value selected as a function of the sensitivity which can be determined by using equation (2) and selecting the background current that provides the desired sensitivity. The minimum A/L ratio (a very small passage) that can be used is a finite number that can be calculated to provide limited residual oxygen flux diffusion in a reasonable response time. The minimum A/L usable also depends on the ability to manufacture small cross sectional area channels for flux diffusion.

Typically, the flux diffusion path is a narrow annular channel surrounding the cathode, filled with the electrolyte, and the diffusion channel length is measured in axial direction from the electrolyte chamber in which the anode is placed to the cathode surface or plane facing the membrane. The diffusion path for residual oxygen can be formed in other locations such as providing holes through the end of a support for the cathode, or it can comprise a series of holes or channels.

The cathode can be of any other noble metal in addition to gold, such as, rhodium, platinum, silver or similar metals. The anode preferably is silver, but also can be zinc, cadmium, or lead. The electrolyte is selected to be compatible with the cathode and anode materials selected.

The preferred membrane material is Teflon (Polytetrafluoroethylene or PTFE), but it can be other desired membrane materials that serve the same function.

DETAILED DESCRIPTION OF THE ILLUSTRATIVE EMBODIMENTS

The present invention relates to a dissolved oxygen sensor for monitoring water quality. The sensor is designed to have a reduced level of background current, to permit sensing low levels of oxygen in water. The background current is generated when an electrical potential is applied between an anode and cathode which are immersed in an electrolyte in the sensor. The present invention controls the background current by properly shaping and sizing a channel from the electrolyte stored in a chamber of the sensor to the cathode, so the effect of residual oxygen in the electrolyte, which causes the background current, is reduced.

Figure 1:
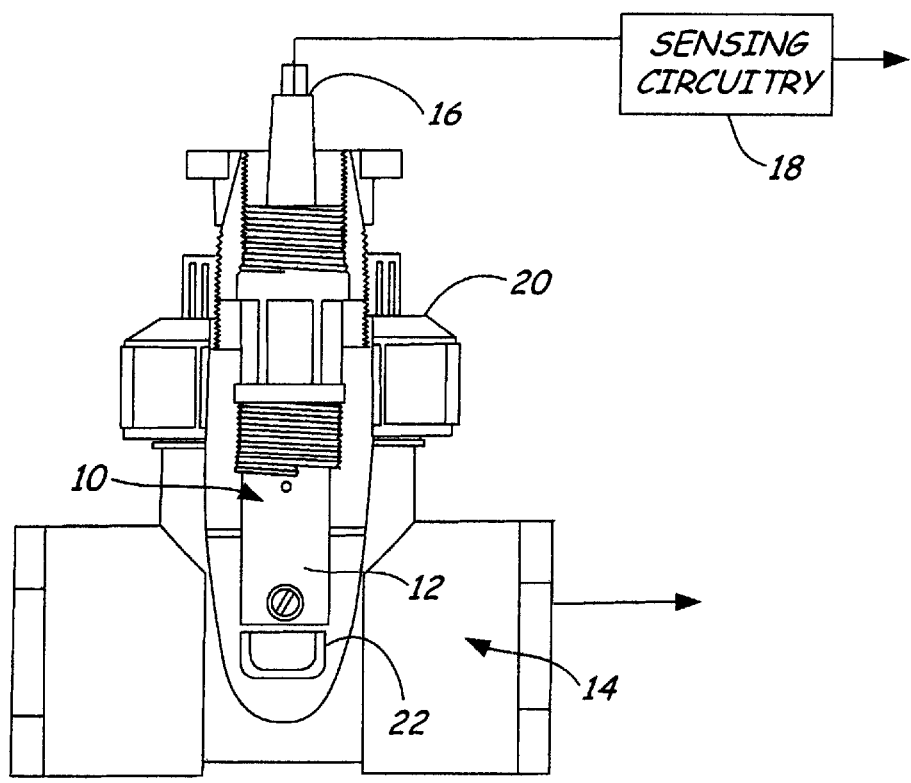
FIG. 1 is a schematic representation of a typical pipe connector housing a dissolved oxygen (DO) sensor made according to the present invention.

In FIG. 1, a dissolved oxygen sensor indicated generally at 10 includes an outer tubular housing 12 that mounts in a T-connection or fitting 14. The sensor cable 16 connects to suitable sensing circuitry 18 that provides the output signal. The output signal can be used in a transmitter to control a process or can be provided to an indicator showing the dissolved oxygen in the liquid passing through the fitting 14. The outer housing 12 of the sensor 10 is held in place with a coupling nut 20. An end portion 22 of the sensor protrudes into the fluid stream of aqueous liquid material, such as water, that flows through the fitting 14. A cathode support sleeve 32 is mounted inside the housing 12, and a cathode 34 is positioned at an outer end of the support sleeve and has a surface facing the membrane 30. A lead 36 carries a voltage or potential to the cathode in a normal manner.

Figure 2:
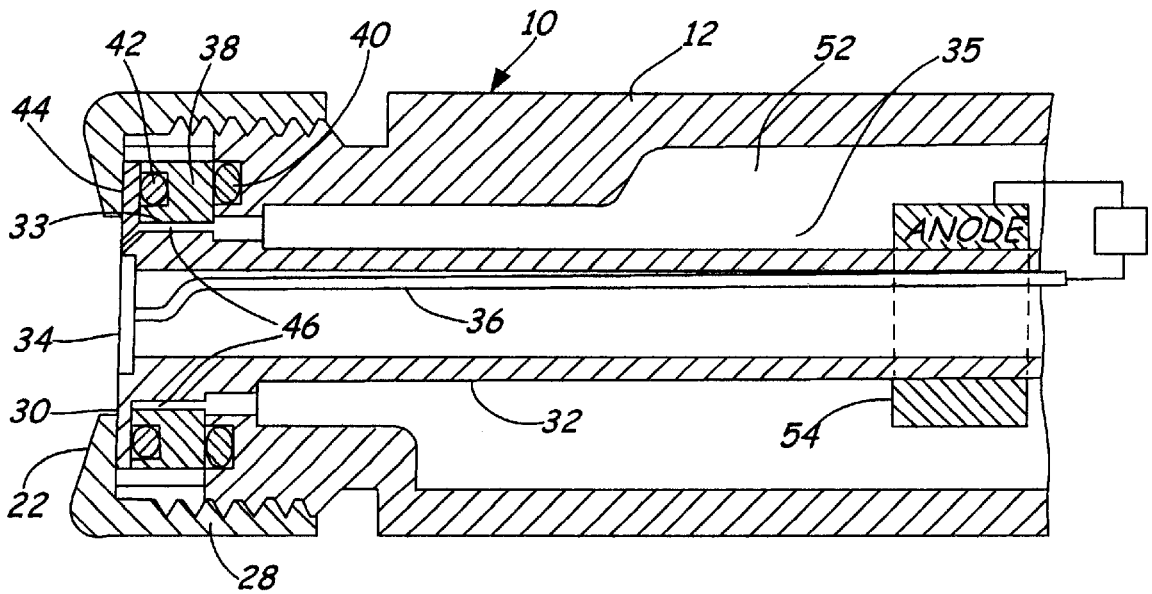
FIG. 2 is a cross sectional view of a DO sensor including features of the present invention.

As shown in FIG. 2, an outer nut 28 fits over the end of the outer housing 12 and is used to hold a membrane 30 over the open end of the housing. The membrane 30 is clamped between a spacer ring 38 and a clamp ring 44 that are clamped together with the nut 28. The surface of the spacer ring 38 opposite from the membrane is sealed relative to the end of housing 12 with an O ring 40 in a groove in the housing. The spacer ring 38 also carries an O ring 42 that engages membrane 30. The clamp plate 44 bears on the membrane 30 to force it against the O ring 42 and the spacer ring 38 to hold the membrane in position.

Figure 3:
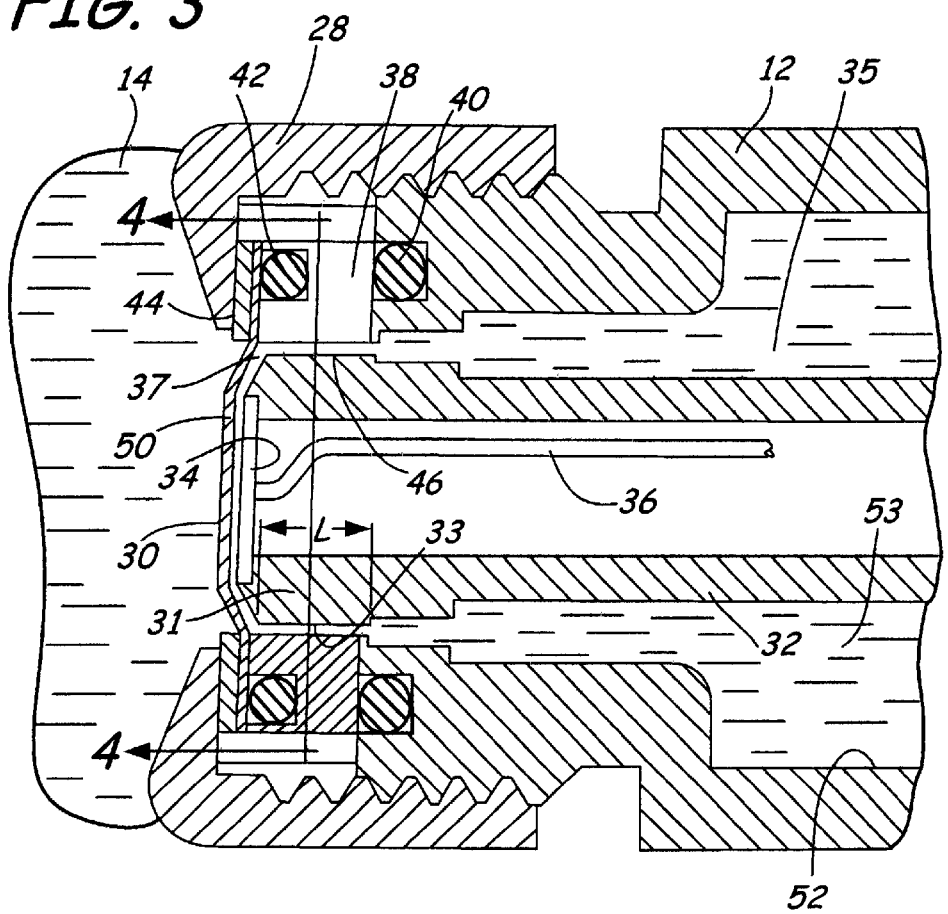
FIG. 3 is an enlarged cross sectional view of the membrane and cathode of the sensor FIG. 1 illustrating a typical diffusion channel for the oxygen flux.

The outer end portion 31 of cathode support sleeve 32 has an outer surface 33 (see FIG. 3) that is inside the inner surface 37 of a center opening of spacer ring 38. The outer surface 33 of sleeve 32 and the inner surface 37 of the opening in spacer ring 38 form a narrow, axially extending annular channel 46 that surrounds the outer end portion of the cathode support sleeve, as shown in FIG. 3.

The restricted residual oxygen flux channel 46 has a diffusion path length L in a direction along the central longitudinal axis of the sensor from the electrolyte filled chamber 52 to the space 50 between the cathode surface and the membrane. An anode represented at 54 is positioned in chamber 52 and is immersed in the electrolyte. There is a thin layer of electrolyte in the space 50 between the membrane 30 20 and the facing surface of cathode 34, as shown in FIG. 3.

Figure 4:
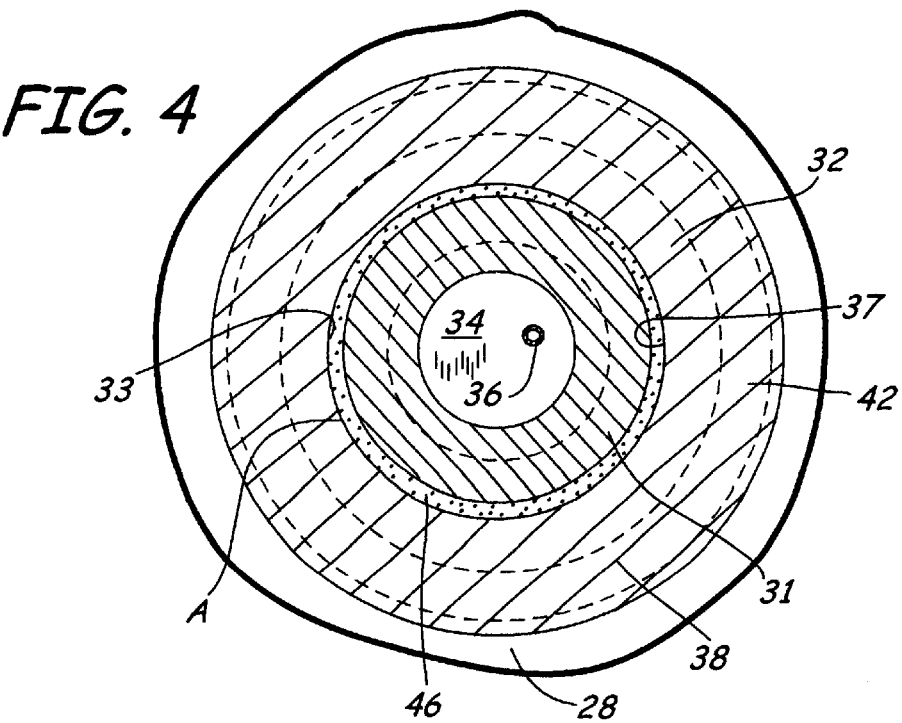
FIG. 4 is an end view of the cathode and diffusion channel taken on line 4—4 in FIG. 3.

When the sensor starts to operate by applying a potential represented at V between the anode and cathode, oxygen will be reduced through the electrochemical process, which generates a diffusion of residual oxygen flux toward the cathode through the restricted channel 46. Channel 46 has an area "A", as shown in FIG. 4, that is calculable and can be selected by the designer, and a length "L" shown in FIG. 3 that is also selectable. Both the area and length of the channel are thus known. When the residual oxygen in the electrolyte is reduced and the output signal is at a steady state, and no oxygen is passing through membrane 30, for example when placing the sensor in deaerated water, the steady state current detected by circuit 18 is the constant background or offset current caused by the residual oxygen in the electrolyte.

In order to reduce the background current, the present invention provides a structure and a method of maintaining the ratio of the area of the restricted flux diffusion channel to the length of the flux diffusion channel small enough so that the background current is maintained at a desired low level.

It is known that with prior art amperometric sensor design the current output at 8 ppm dissolved oxygen can be designed to be about 40 $\mu$A. In such a case, since the sensor output is linear, an arithmetical ratio shows that background current below 5 $\eta$A will provide a sensing accuracy of ±1 ppb.

Figure 5:
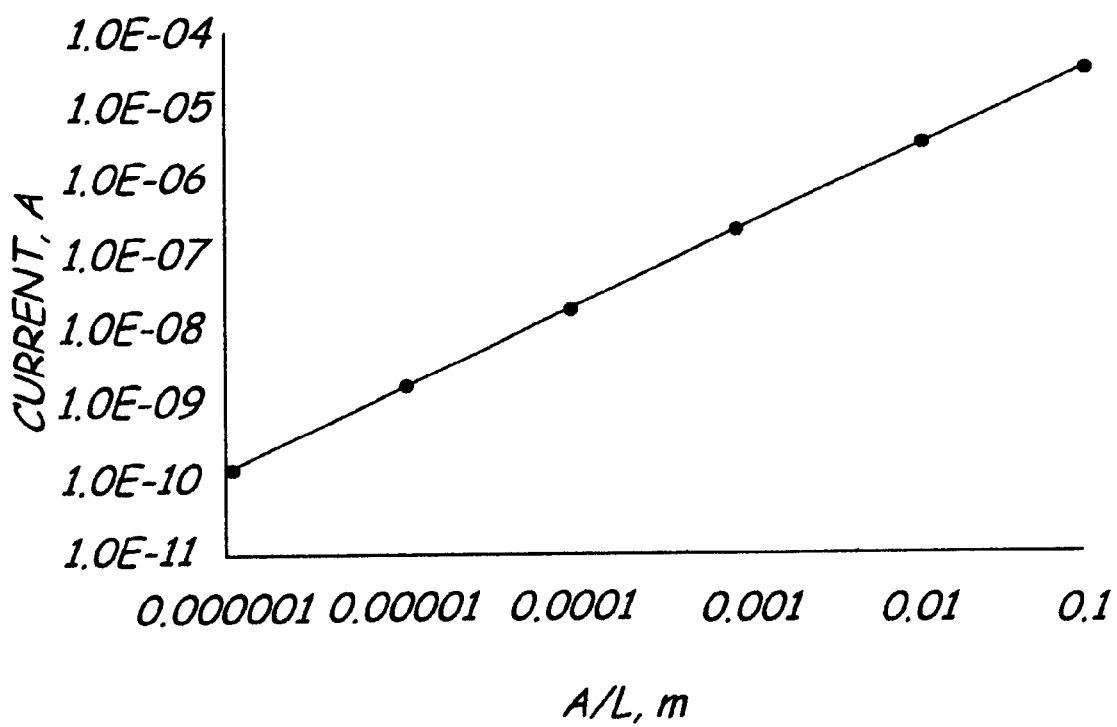
FIG. 5 is a graphical representation of the plot of background current versus the A/L ratio, based upon Equation (2).

Referring to FIG. 5 and the graphical representation plotting the background current versus A/L, the A/L value needs to be below 0.026 mm in order to meet this criteria. The plot of FIG. 5 is based on equation (2).

In one example, a dissolved oxygen sensor having an A/L ratio around 0.009 was prepared. It was filled with an electrolyte, and subjected to a suitable potential, and after about 5 hours, the sensor output reached a stable value around 1.8 $\eta$A which is the background or offset current. This is very close to the calculated value 1.7 $\eta$A from Equation 2, and proves the concept of reducing the background current by having a low A/L ratio.

The minimum A/L ratio is one that will permit diffusion of oxygen flux in a reasonable length of time at start up. It has been found that very quick start up is achieved with the present invention because of the low background or offset current, because it brings a fast "come down speed" after the sensor is calibrated in air and placed back to oxygen free media. The simple design of the present invention makes it more easily manufactured, and maintainable than the guard ring electrode design.

The maximum A/L for a given sensor can be selected on the basis of the sensing accuracy desired. Background or offset current can be maintained at or below the selected level.

The present method includes selecting a desired background current to meet a desired sensing accuracy, for example, 5 $\eta$A that meets a sensing accuracy of ±1 ppb for a normal size cathode. For different desired levels of background current, the A/L ratio is kept below other selected maximum levels.

The area of the diffusion channel or passage for residual oxygen in the electrolyte can be selected, and then the length will be determined from equation (2). If the length of the diffusion channel is a set length, the area of the channel that is needed to obtain the desired ratio can be calculated from Equation (2).

The discovery of the effect of a proper A/L ratio of the residual oxygen diffusion path in reducing the background current can be applied to a range of different sizes of amperometric sensors. The size of the cathode and other factors can be taken into consideration as needed by persons skilled in the art.

The present invention, thus, teaches reducing background or stand off current and fast come down speed without added components, such as a guard ring electrode.

Although the present invention has been described with reference to preferred embodiments, workers skilled in the art will recognize that changes may be made in form and detail without departing from the spirit and scope of the invention.

What is claimed is:

1. A method for sensing presence of a gas in a liquid, comprising:

forming a sensor housing with an open end and a chamber;

mounting an anode and a cathode in the sensor housing;

connecting the anode and cathode to a potential V to generate a sensor output current;

covering the open end with a membrane having a first side facing the cathode and a second side in contact with the liquid;

providing chamber electrolyte contacting the anode in the chamber;

providing a channel between the cathode and the chamber electrolyte, the channel having inner and outer channel walls;

providing channel electrolyte standing in the channel of length L and cross sectional area A between the cathode and the chamber electrolyte; and the channel electrolyte controlling a background sensor current level $I_b$; and selecting an area to length A/L ratio less than 0.026 mm so that the channel resistance is high enough to control the background sensor current level $I_b$ to below 5 nanoamperes per 40 microamperes of the sensor output current at a gas concentration of 8 ppm in the liquid to provide a sensing accuracy of approximately +−1 part per billion.

2. The method of claim 1, further comprising:

forming the membrane of a material that is permeable to oxygen to provide a dissolved oxygen sensor.

3. The method of claim 1, further comprising:

forming the channel as an annular shape surrounding the cathode.

4. The method of claim 1, further comprising:

forming the membrane of polytetrafluoroethylene.

5. A method of providing dissolved oxygen concentration sensing down to 1 part per billion in an amperometric oxygen sensor that includes an anode and a cathode, an electrolyte coupled along a path between the anode and the cathode, a potential source coupled to the anode and cathode to provide an output current, and a membrane separating the cathode from a liquid in which the oxygen is dissolved, the method comprising:

designing the amperometric oxygen sensor to provide an output current of at least 40 microamperes in response to a dissolved oxygen concentration of 8 parts per million;

providing a diffusion channel along the path between the anode and the cathode, the diffusion channel having a length L along the path and a cross sectional area A transverse the path, providing an area to length ratio of A/L for the path; and controlling a background current portion of the output current to less than 5 nanoamperes, where the background current portion corresponds to less than 1 part per billion of oxygen concentration in the liquid, by setting the area/length ratio of the diffusion channel to less than 0.026 mm to deplete residual oxygen adjacent the cathode.

6. The method of claim 5, wherein the background current portion of the output is maintained below 5 nanoamperes without the use of an electrode guard ring to deplete residual oxygen around the cathode.

7. The method of claim 5, further comprising:

forming the diffusion channel as a annular space between an outer surface of a cathode support sleeve and an inner surface of a spacer ring.

* * * * *